United States Patent [19]

Patrick et al.

[11] Patent Number: 5,076,429

[45] Date of Patent: Dec. 31, 1991

[54] SHARPS CONTAINER

[75] Inventors: Milton L. Patrick, San Diego, Calif.; Lilee S. Gelinas, Colleyville, Tex.; Carla L. Hansen, Moorhead, Minn.; Patti Boman, Carthage, Mo.

[73] Assignee: Voluntary Hospitals of America, Irving, Tex.

[21] Appl. No.: 681,642

[22] Filed: Apr. 5, 1991

Related U.S. Application Data

[63] Continuation of Ser. No. 442,217, Nov. 28, 1989, abandoned.

[51] Int. Cl.$^5$ .............................................. B65D 83/10
[52] U.S. Cl. .................................... 206/370; 206/366; 220/252; 220/908; 220/335
[58] Field of Search ............... 206/363, 365, 366, 370; 220/908, 213, 252, 335

[56] References Cited

U.S. PATENT DOCUMENTS

| | | | |
|---|---|---|---|
| 697,655 | 4/1902 | O'Leary | 220/252 |
| 1,169,606 | 1/1916 | Blank et al. | |
| 1,333,051 | 3/1920 | Young | 220/252 |
| 1,638,360 | 8/1927 | Olson | |
| 1,875,690 | 9/1932 | Adams | |
| 2,326,886 | 8/1943 | Rathbun | |
| 2,986,328 | 5/1961 | Delas | |
| 3,249,294 | 5/1966 | Hughes et al. | |
| 3,724,400 | 4/1973 | Steiber | |
| 3,749,274 | 7/1973 | Mele et al. | |
| 4,032,037 | 6/1977 | Dubery et al. | |
| 4,303,172 | 12/1981 | Bosland | 220/252 |
| 4,315,592 | 2/1982 | Smith | |
| 4,453,648 | 6/1984 | Harris et al. | |
| 4,488,643 | 12/1984 | Pepper | |
| 4,494,652 | 1/1985 | Nelson et al. | |
| 4,580,688 | 4/1986 | Harris et al. | |
| 4,662,516 | 5/1987 | Baker, Sr. et al. | 206/363 |
| 4,714,168 | 12/1987 | Johnson et al. | |
| 4,715,498 | 12/1987 | Hanifl | |
| 4,722,472 | 2/1988 | Bruno | |
| 4,736,860 | 4/1988 | Bemis | |
| 4,779,728 | 10/1988 | Hanifl et al. | |
| 4,804,090 | 2/1989 | Schuh et al. | 206/366 |
| 4,809,850 | 3/1989 | Laible et al. | 206/366 |
| 4,828,107 | 5/1989 | Spencer | 206/366 |
| 4,842,138 | 6/1989 | Sandel et al. | 206/370 |
| 4,874,103 | 10/1989 | Quisenberry et al. | 206/366 |
| 4,890,733 | 1/1990 | Anderson | 220/335 |

FOREIGN PATENT DOCUMENTS 595503 12/1947 United Kingdom .
720056 12/1954 United Kingdom .

OTHER PUBLICATIONS

PRO-TEC Containers, Inc., Sales Literature describing Disposable Sharps Containers, distributed prior to Jun. 1, 1988.
American Hospital Supply Corporation Sales Literature describing a sharps disposal system, dated 1986.
Sage Products, Inc., Sales Literature describing a sharps disposal system, dated 1987.
Bemis Health Care Sales Literature describing the MEDX Universal sharps disposal containers, undated.
Premium Plastic, Inc., Sales Literature describing the Roll-a-Way 2001 sharps disposal system, distributed prior to spring 1988.
Becton-Dickinson Sales Literature describing the "Monoject" sharps container, dated 1987.
Concord Laboratories, Inc. Sales Literature describing the "Sharpsafe" waste containment system, undated.
Winfield Corporation Sales Literature describing the "Sharpsguard 2000", undated.

Primary Examiner—David T. Fidei
Attorney, Agent, or Firm—Kirkland & Ellis

[57] ABSTRACT

There is provided a sharps container comprising a receptacle and a lid engaging the receptacle, the lid including a rotatable tray and a baffle flap for sealing the receptacle when the tray is in an open position. The tray is biassed toward the open position by the force of gravity, and one or more detents may be provided to hold the tray selectively in a closed or partially closed position.

7 Claims, 5 Drawing Sheets

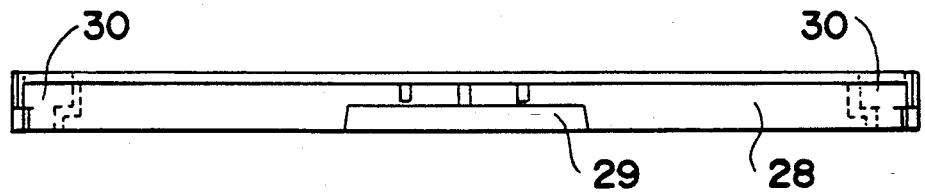
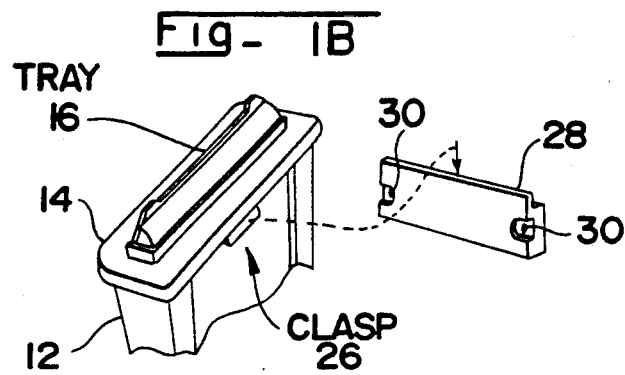
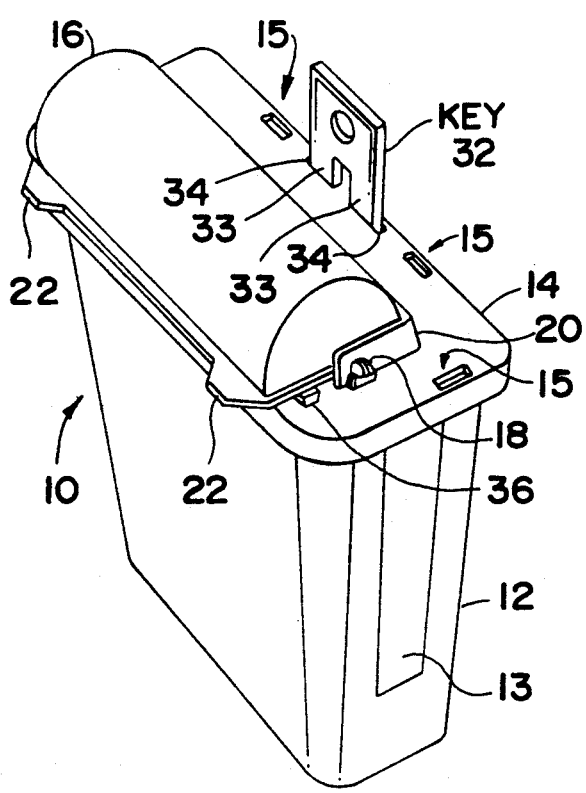
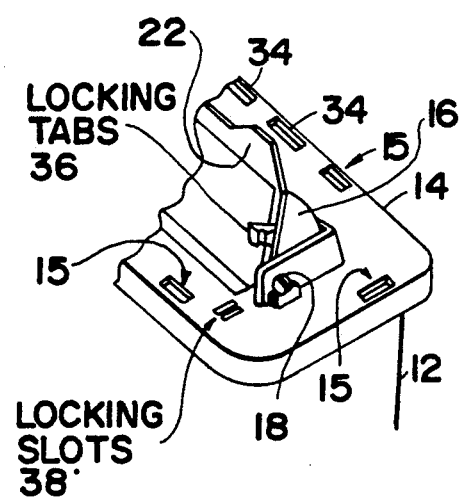

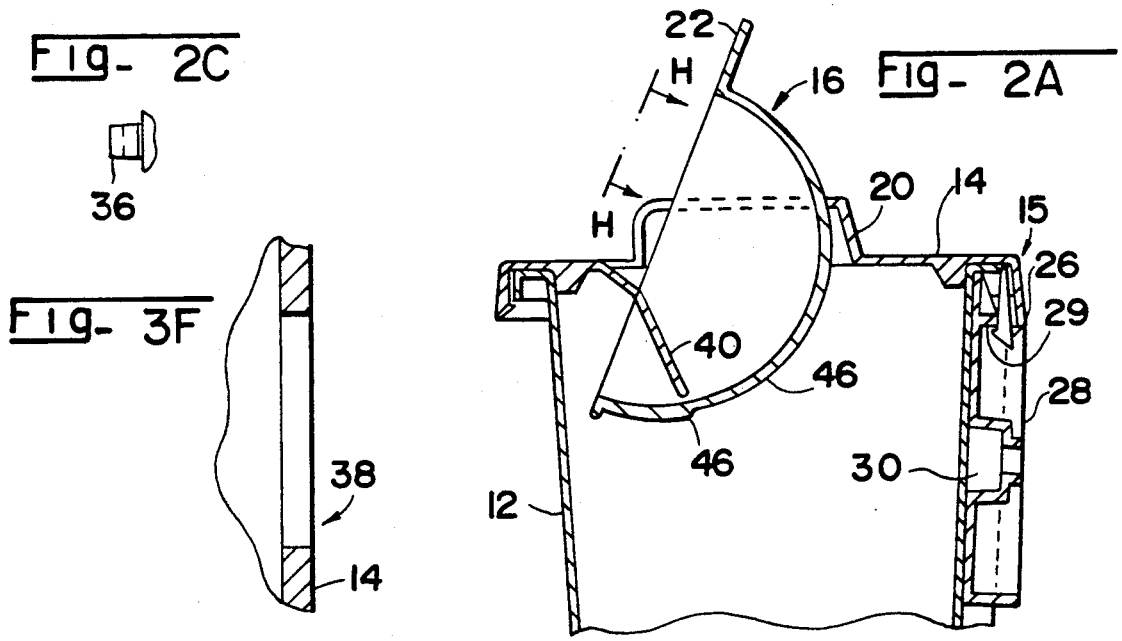
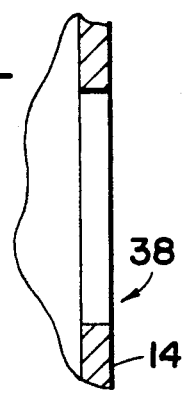
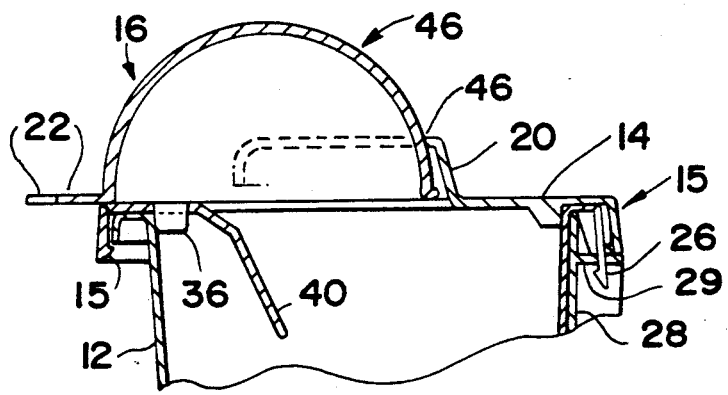
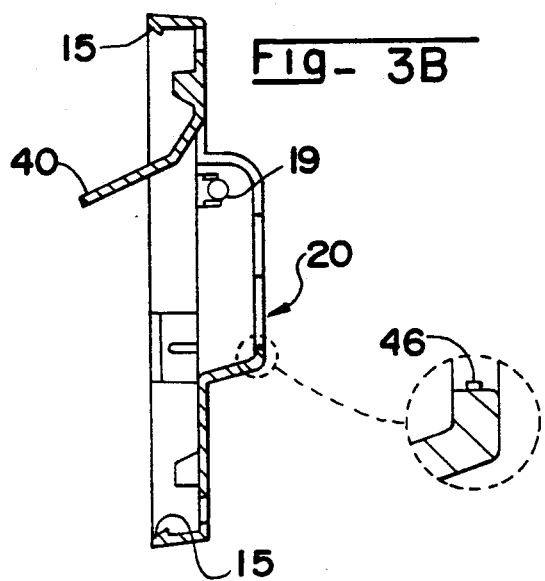

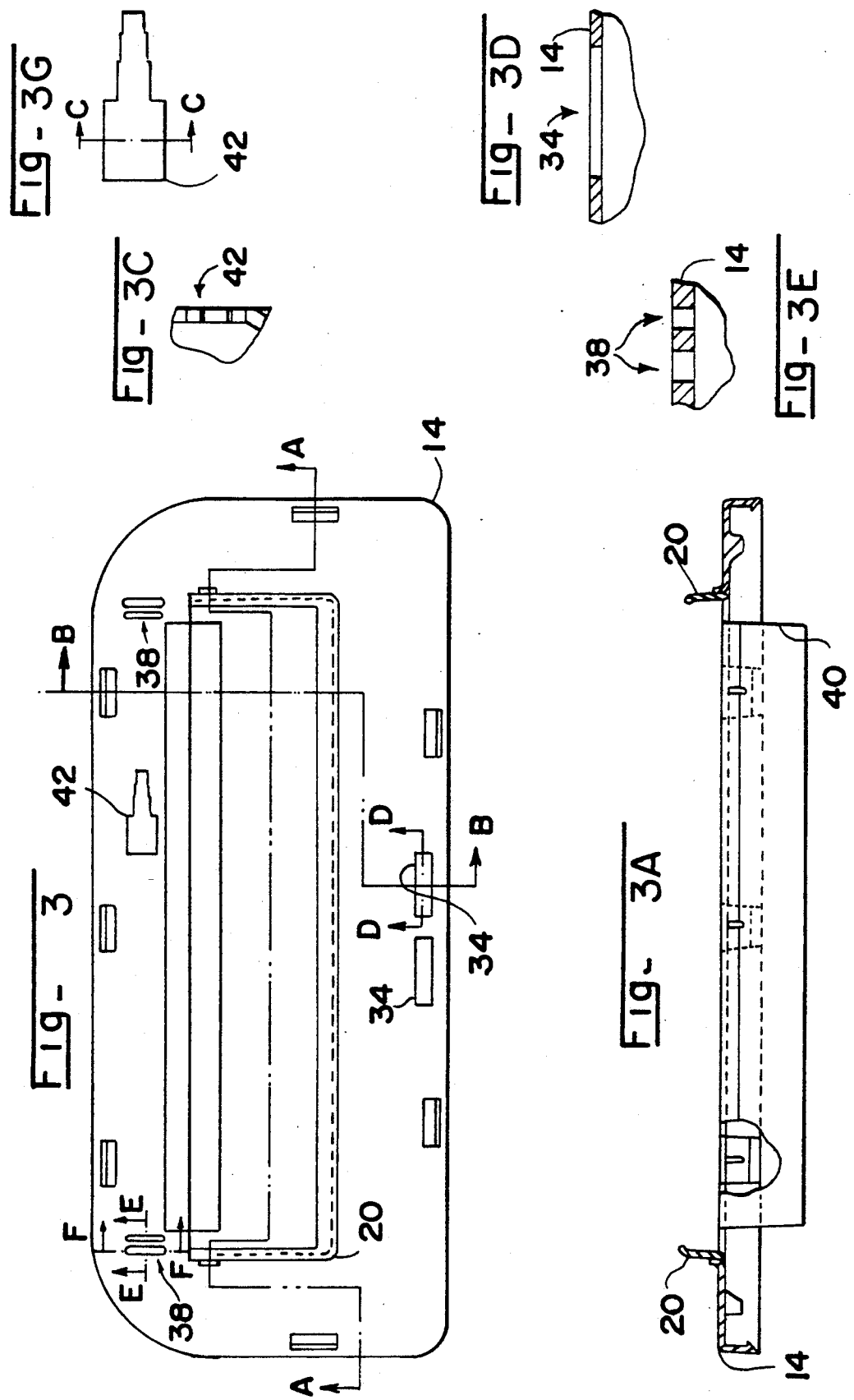

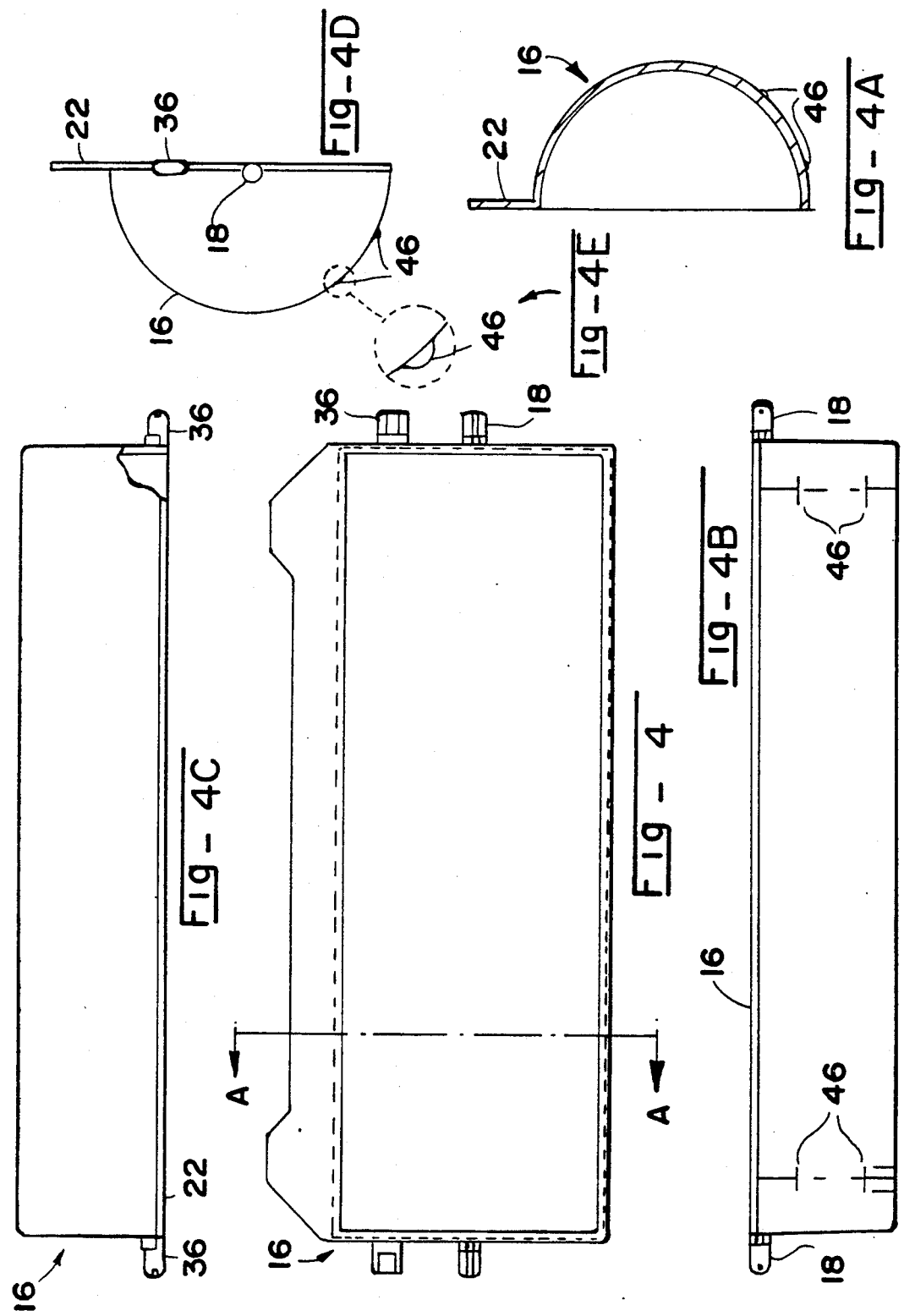

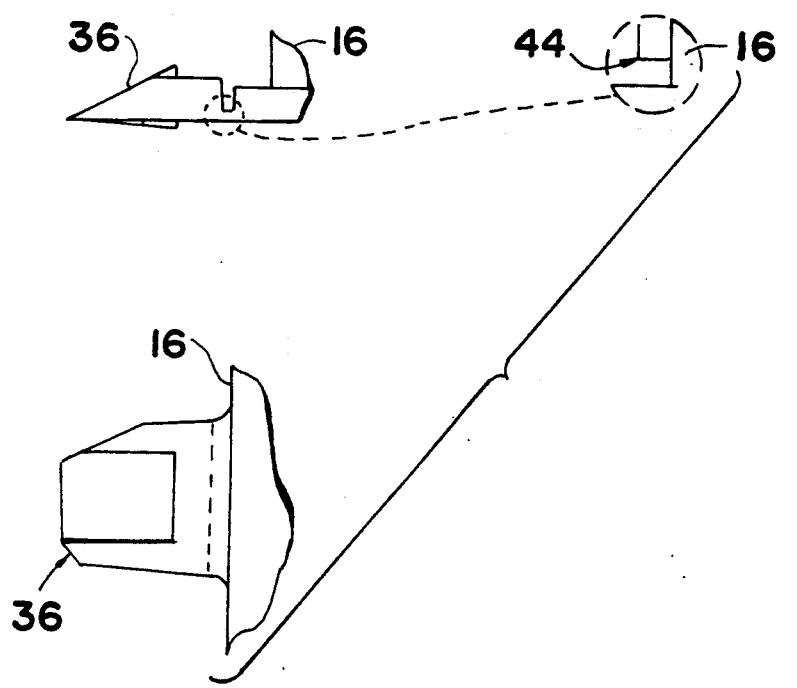
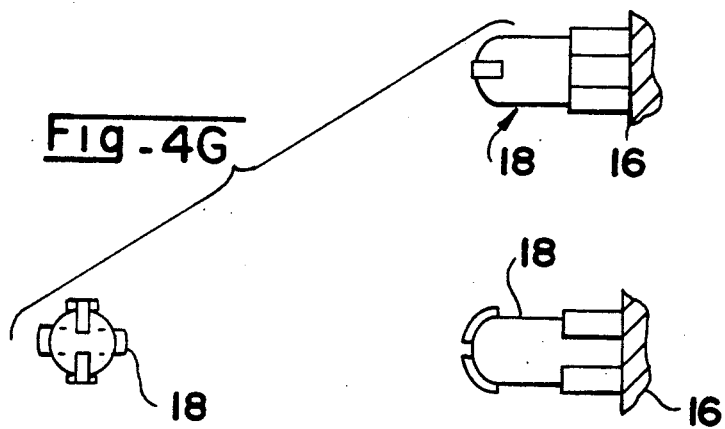

SHARPS CONTAINER

This is a continuation of copending application Ser. No. 07/442,217 filed on Nov. 28, 1989 now abandoned.

BACKGROUND

The present invention relates to containers, and more particularly to containers for sharp objects, or "sharps", such as used hypodermic syringes and other medical supplies.

In hospitals and other medical facilities, it is necessary to provide receptacles for used sharps that inhibit access to the interiors of the receptacles and prevent withdrawal of the sharps previously deposited in them. Also, the receptacles must not leak when they are in upright or typical-use positions. Those features are highly desirable to prevent injuries and the spread of disease that could occur due to the improper handling of used sharps. At the same time, the disposal of an item in the receptacle should be a simple process requiring a minimum of complicated hand motions; preferably, the act of disposal should be a one-hand operation.

Many receptacles have been disclosed that provide the foregoing conflicting features to various extents. Among those are the containers described in U.S. Pat. Nos. 4,779,728 to Hannifl et al.; 4,736,860 to Bemis; 4,715,498 to Hannifl; 4,714,168 to Johnson et al.; and 4,580,688 to Harris et al. All those prior receptacles fail to provide the combination of features and the advantages of the present invention. For example, the container disclosed in the patent to Bemis requires both hands or awkward motions of one hand to operate: the user must first open the container door which is biassed shut, then place the used sharp in the door cradle, and finally shut the door, thereby dumping the cradle contents into the container. The container disclosed in the patent to Johnson et al. has a normally open door, but the interior of the container is not completely enclosed when the door is open.

SUMMARY

In accordance with the present invention, there is provided a sharps container comprising a receptacle and a lid engaging the receptacle, the lid including a rotatable tray and a baffle flap for sealing the receptacle when the tray is in an open position. The tray is biassed toward the open position by the force of gravity, and one or more detents may be provided to hold the tray selectively in a closed or partially closed position.

A container as described above provides many advantages over prior sharps containers. Their components being nestable saves transport and storage space; their components are easy to assemble and carry by one person; and, very importantly, one person can easily operate the container to dispose of contaminated sharps and lock the container closed when it is full.

BRIEF DESCRIPTION OF THE DRAWINGS

The present invention will be understood after a reading of the following detailed description in conjunction with the drawings in which:

FIG. 1A is a perspective view of a container in accordance with the present invention;

FIGS. 1B and 1C are partial perspective views of the container;

FIG. 1D is a top view of a wall-mounting bracket;

FIGS. 2A and 2B are partial cross-section views of the container with the tray in the open and closed positions, respectively;

FIG. 2C is a partial section of the tray;

FIGS. 3, 3A, 3B, 3C, 3D, 3E, 3F and 3G are views of the lid of the container; and FIGS. 4, 4A, 4B, 4C, 4D, 4E, 4F and 4G are views of the tray of the container.

DETAILED DESCRIPTION

Referring now to the drawings in which like parts are identified by like reference numerals throughout, FIG. 1A shows a perspective view of a container 10 seen in more detail in the other figures. The assembled container 10 is advantageously fabricated through conventional molding of a semi-opaque thermoplastic material such as polypropylene and comprises a rigid, hollow receptacle portion, or bucket, 12 and a rigid cover portion, or lid, 14. The bucket and lid are fabricated and may be transported separately, minimizing the storage and transport space required because several buckets can be nested together, as can several lids. When ready for use, the lid 14 is permanently attached to the bucket 12 by any suitable means, such as a plurality of one-way snap fastenings, or barbs, 15 that are integral with lid 14 and that snap over the rim of bucket 12.

The lid 14 includes a tray 16 in registration with an opening through the lid. The tray 16 is manually moveable between closed and open positions and is preferably biassed toward the open position (shown, for example, in FIG. 2A). This bias can be achieved in many ways, such as a spring assembly, elastomeric band, etc., but preferably it arises from gravity alone acting on the tray 16, as in the embodiment shown in the figures.

As seen, for example, in FIG. 1A, tray 16 may be partially cylindrical; it rotates about a horizontal axis through two cylindrical axle projections 18 that are located on its opposite sides and are received in matching bores 19 in an upstanding lip 20 on lid 14. Axle projections 18 are shown in more detail in FIG. 4G, and one such bore 19 can be seen in FIG. 3B. The location of the rotational axis defined by axle projections 18 with respect to the center of gravity of tray 16 is advantageously selected so that gravity constantly forces tray 16 toward the open position of FIG. 2A. Tray 16 may further include one or more flats 22 which serve as a handle for moving tray 16; two such flats 22 are preferably provided, thereby facilitating one-handed operation with either hand of the tray 16. Thus, tray 16 forms a convenient open receptacle into which contaminated sharps can be dropped for disposal. It will be appreciated that partial rotation of tray 16 toward the closed position will drop the contaminated sharps into bucket 12, and gravity will return tray 16 to the open position when tray 16 is released.

Container 10 is preferably suspended from a wall or other flat vertical surface through the cooperation of a one-way snap fastening comprising a clasp 26 on lid 14 and a wall bracket 28 having a lip 29, as illustrated in FIGS. 1B, 1D, 2A and 2B. The wall bracket 28 can be secured to the wall in any convenient fashion, such as two screws located in depressions 30 in wall bracket 28. Container 10 is installed on wall bracket 28 by placing the clasp 26 on lid 14 over the top edge of the wall bracket 28, then moving the container downward until clasp 26 snaps over a suitable lip 29 on bracket 28 (see FIGS. 2A and 2B). Lip 29 advantageously has a tapered vertical cross-section (seen most clearly in FIGS. 2A and 2B) to facilitate movement of clasp 26 onto bracket 28. Moreover, the rear wall of bucket 12 may include a suitable recess for accommodating the bracket 28 and providing sideward stability to the hanging container through a tapering engagement of the sides of bracket 28 with the sides of the bucket's recess.

When container 10 is full or otherwise ready for disposal, the container 10 can be removed from the wall by inserting a key 32 having at least two prongs 33 into key slots 34 and pulling the top of key 32 in a direction away from and perpendicular to the wall while simultaneously lifting the container 10, preferably from the bottom. The multi-pronged key thereby temporarily moves clasp 26 toward the wall, away from the wall bracket 28 and lip 29, allowing the container 10 to be removed. Clasp 26 is suitably dimensioned so that a single-prong key or other object inserted into only one of key slots 34 will not fully release clasp 26 from the bracket 28 and lip 29. Thus, all of the plurality of prongs 33 must be simultaneously inserted into key slots 34 to release the container from the bracket 28.

Similar one-way snap fastenings permit the tray 16 to be locked to the lid 14 in the closed position. These fastenings advantageously comprise bendable tabs 36 on tray 16 that engage sets of tab slots 38 in lid 14; one such fastening is illustrated in, for example, FIGS. 1C and 2C. Tray 16 is supplied with tabs 36 normally positioned as illustrated in FIG 1A, permitting free manual opening or closing of tray 16. When the container is full or is to be removed, tabs 36 are bent to a locking position; the tray 16 is then closed with the tabs 36 so oriented, forcing the tabs 36 through the outer pair of two sets of tab slots 38. Tabs 36 are preferably oversized with respect to tab slots 38, and the inner and outer slots form a rib that deflects as the locking tabs 36 snap through the outer slots, locking the tray closed.

Referring for example to FIGS. 2A and 2B, access to the contents of the container 10 is restricted by the cooperation of a baffle flap 40 which projects downward from lid 14 which is appropriately dimensioned with respect to the tray 16 to seal the container contents when the tray 16 is in the partially closed or open positions. Besides providing effective sealing of the container, the baffle flap 40 and rotatable tray 16, by the rotation of tray 16 through the interior of bucket 12, advantageously provide an indication of the level of the container's contents and ensure that the container 10 cannot be overfilled. If desired, one or more partially transparent portions may be formed on the semi-opaque bucket 12, e.g., by polishing an area 13 on one of the semi-opaque sidewalls of bucket 12, through which the level of the contents of the container 10 can be visually determined (see FIG. 1A). It will be appreciated that polypropylene is normally semi-opaque, although it can also be rendered suitably semi-opaque by adding a small proportion of a colorant and/or by texturing the surface. It will also be appreciated that a clear view to the interior of bucket 12 (and its used contents) is unnecessary to determine the level of its contents.

FIGS. 3, 3A-3G show plan, section and detail views of lid 14 as above-described. Referring in particular to FIGS. 3C and 3G, there is shown a convenient means for removing the needles from syringes or other medical devices comprising an aperture 42 in lid 14 having a plurality of sections, each section having a cross-dimension corresponding to various medical devices. Once detached, the needles are received in bucket 12 in which they can be safely discarded.

FIGS. 4, 4A-4D and 4F-4G similarly show orthogonal and section and detail views of tray 16. Referring in particular to FIG. 4F, there are shown orthogonal and detail views of the bendable tabs 36 for locking the tray 16 closed. As shown, tab 36 is integrally formed with tray 16 and is rendered bendable with respect to the relatively thicker tray by a thin hinge section 44. FIG. 4G shows orthogonal views of axle projections 18.

Shown in detail in FIG. 4E are detent tabs 46 that comprise small protrusions on tray 16. Detent tabs 46 selectively engage similar detent tabs 46 on the upstanding lip 20 on lid 14 to lightly hold the tray in position with respect to the lid. In the preferred embodiment of the invention, two sets of detent tabs 46 are provided on tray 16 as indicated in the figures by which the tray 16 can be temporarily held in either closed or partially closed positions. The dimensions of detent tabs 46 are preferably such that a simple tap on either of tray flats 22 will release tray 16 from restraint by the detent tabs 46. When such a tap is delivered with the tray in the closed or partially closed positions, the tray will move by gravity toward the open position. The tray is thus biassed toward the open position with detents provided for users who may want the tray partially or fully closed after depositing contaminated sharps.

The foregoing description is intended in all senses to be illustrative and not restrictive. Variations and modifications will occur to those of ordinary skill in the art to which the invention pertains, and those variations and modifications that fall within the spirit and scope of the invention, as it is defined by the appended claims, are fully intended to be included therein.

What is claimed is:

1. A sharps container comprising:
    a receptacle for receiving sharps;
    a lid engaging the receptacle, the lid including a tray having a partially cylindrical cross-section disposed thereon and rotatable about a horizontal axis between fully open and fully closed positions and a baffle flap projecting into the interior of the receptacle, dimensioned with respect to the tray for sealing the receptacle when the tray is in the fully open position,
    wherein the tray can be selectively biased toward the fully open position or held in the fully closed position and the tray completely seals the receptacle when the tray is in the fully closed position; and
    means for selectively holding the tray in at least one position between the fully open and fully closed positions, in addition to biassing the tray in the fully open position and holding the tray in the fully closed position.

2. The sharps container of claim 1, wherein the lid and the tray include selectively engageable detent tabs for retaining the tray in at least one predetermined partially open position, such that when the tray is in the partially open position, sharps may be safely discarded by placing the sharps into the tray, from which the sharps slide directly into the receptacle.

3. The sharps container of claim 2, wherein the lid and tray include a plurality of selectively engageable detent tabs for retaining the tray in either the closed position or a partially closed position, wherein the dimensions of the detent tabs are such that a tap on the tray will release the tray from restraint by the detent tabs.

4. The sharps container of claim 1, wherein the tray is biased toward the open position by gravity.

5. A sharps container comprising:
a receptacle for receiving sharps; and
a lid engaging the receptacle, the lid including a tray having a partially cylindrical cross-section disposed thereon and rotatable about a horizontal axis between fully open and fully closed positions and a baffle flap projecting into the interior of the receptacle, dimensioned with respect to the tray for sealing the receptacle when the tray is in the fully open position,
wherein the tray is biassed toward the fully open position and the tray completely seals the receptacle when the tray is in the fully closed position,
and wherein the tray and the lid include means for locking the tray in the fully closed position comprising
at least one bendable tab comprising a thin hinge section about which the tab can be bent, and
at least one slot corresponding to each bendable tab,
wherein the bendable tab is bent from a non-locking position against the lid, to a locking position projecting away from the lid for engaging the corresponding slot and locking the tray in the fully closed position.

6. A sharps container comprising:
a receptacle for receiving sharps; and
a lid engaging the receptacle, the lid including a tray having a partially cylindrical cross-section disposed thereon and rotatable about a horizontal axis between fully open and fully closed positions and a baffle flap projecting into the interior of the receptacle, dimensioned with respect to the tray for sealing the receptacle when the tray is in the fully open position,
wherein the tray is biased toward the fully open position and the tray completely seals the receptacle when the tray is in the fully closed position,
and wherein the tray and the lid include means for locking the tray in the fully closed position comprising:
at least one bendable tab comprising a thin hinge section about which the tab can be bent;
one pair of slots corresponding to each bendable tab; and
a rib formed between each pair of slots,
wherein the bendable tab can be bent to a locking position for locking the tray in the fully closed position by deflecting the rib formed between each pair of slots and engaging the slots.

7. The sharps container of claim 1, further comprising a bracket mountable to a wall, wherein the receptacle includes a clasp for suspending the container from the bracket, and the clasp engages the bracket and is releasable therefrom by simultaneous movement of the clasp by a plurality of prongs.

* * * * *